United States Patent
Schiller et al.

(10) Patent No.: US 6,900,009 B2
(45) Date of Patent: May 31, 2005

(54) METHOD FOR CREATING A FROZEN TISSUE ARRAY

(76) Inventors: Bernice Schiller, 2150 Center Ave., Fort Lee, NJ (US) 07024; Stephen Mastorides, 7216 Wareham Dr., Tampa, FL (US) 33647; Carlos Cordon-Cardo, 860 United Nations Plz., 14F, New York, NY (US) 10017

( * ) Notice: Subject to any disclaimer, the term of this patent is extended or adjusted under 35 U.S.C. 154(b) by 499 days.

(21) Appl. No.: 10/006,759

(22) Filed: Dec. 10, 2001

(65) Prior Publication Data

US 2002/0127631 A1 Sep. 12, 2002

Related U.S. Application Data

(60) Provisional application No. 60/250,084, filed on Nov. 30, 2000.

(51) Int. Cl.$^7$ ................................................. C12N 5/00
(52) U.S. Cl. ....................... 435/1.3; 435/40.5; 435/176; 435/177
(58) Field of Search ................................ 435/1.3, 40.5, 435/176, 177

(56) References Cited

U.S. PATENT DOCUMENTS

| 6,406,840 B1 | * | 6/2002 | Li et al. | ....................... 435/1.3 |
| 2002/0009767 A1 | | 1/2002 | Muraca | ..................... 435/40.5 |
| 2002/0094533 A1 | * | 7/2002 | Hess et al. | ...................... 435/6 |

* cited by examiner

Primary Examiner—Leon B. Lankford, Jr.
(74) Attorney, Agent, or Firm—Benjamin Aaron Adler (57) ABSTRACT

The present invention provides a method for creating a frozen tissue array. An oil in a liquid form is added into a recipient block containing frozen tissue cores where the oil has a freezing point lower than the freezing point of the tissue cores; and the recipient block containing the oil is cooled to a temperature about equal to or below the freezing point of the oil; the subsequently frozen oil locks the frozen cores in the recipient block. The oil may also be added to the recipient block prior to inserting the frozen tissue cores. The recipient block may be formed using a cryoarray device comprising a mold plate, an ejector plate, mold alignment pins, ejector pins, and cryoarray pins. Such method may be used for preparing frozen sections with multiple tissue specimens for assays such as in-situ hybridization and immunohistochemistry.

18 Claims, 7 Drawing Sheets

(7 of 7 Drawing Sheet(s) Filed in Color)

METHOD FOR CREATING A FROZEN TISSUE ARRAY

CROSS-REFERENCE TO RELATED APPLICATIONS

This application claims benefit of priority of provisional U.S. Ser. No. 60/250,084, filed Nov. 30, 2000, now abandoned.

BACKGROUND OF THE INVENTION

1. Field of the Invention

The present invention relates generally to the field of molecular pathology. More specifically, the present invention relates to a method for creating frozen tissue arrays for subsequent assaying.

2. Description of the Related Art

The implementation of high-throughput genetic technologies, such as oligonucleotide microarrays, generates myriad points of data. The identified potential candidate genes need to be further characterized and selected using a large number of well-characterized tumors and stringent criteria. Tissue microarrays allow for such high-throughput expression profiling of tumor samples, additionally providing information at the microanatomical level.

Sections cut from tissue arrays allow parallel detection of DNA, e.g., by fluorescence in-situ hybridization (FISH), RNA, e.g., by mRNA in-situ hybridization (mRNA ISH) or protein, e.g., by immunohistochemistry (IHC) targets in each of the multiple specimens in the array. Each microarray block can be sectioned up to 200–300 times. Therefore, tens of thousands of tissue microarray sections can be obtained from a set of tissue specimens in one recipient block. This substantially facilitates molecular profiling of very large numbers of cancer tissues and allows the generation of large-scale correlative databases, including clinical information and molecular data (including images), while ensuring that the donor blocks from which the tissue cores are removed can continue to be utilized so that research materials are not destroyed.

In early 1998, Kononen et al. (1) described a tissue microarray "chip" that had been developed for high-throughput molecular profiling of tumor specimens. Tissue microarrays enable rapid in-situ analysis of up to 1000 tumors or other tissues in a single experiment. In the method of Kononen, original tissue sample sources are morphologically representative regions of regular formalin-fixed paraffin-embedded tumor blocks. Core tissue biopsies are taken from individual "donor" paraffin-embedded tumor blocks and precisely arrayed into a new "recipient" paraffin block using a custom built instrument. Thereafter, Bubendorf et al. published data of a survey of gene amplifications during prostate cancer progression by high-throughput fluorescence in-situ hybridization on tissue microarrays (2). The first hand-held paraffin tissue array apparatus was later marketed.

Tissue microarrays consisting of 0.6 mm biopsies of paraffin-embedded tissues have been used for various clinicopathological studies. This size is sufficient for assessing morphological features of the analyzed tissues on many samples. However, the size of the biopsy used in these arrays may not be representative of the whole tumor specimen because of tissue heterogeneity. Additionally, paraffin tissue arrays have distinct limitations in maintaining intact RNA transcription levels, as well as proteins and other molecules (i.e., lipids) due to the fixatives and chemical reagents required for the paraffin process. Thus, tissue microarray technology using paraffin-embedded tissues can reach its limits for the detection of RNA targets or certain proteins. The use of a frozen tissue array or a cryoarray strategy would overcome these limitations and would allow for the processing of multiple frozen tissue specimens and/or cell lines on a single tissue block.

Therefore, it would be beneficial to have an effective means and a system for creating tissue arrays that allow all molecules to be assayed at the expression level and simultaneously visualized at micro-anatomical levels. Specifically, the prior art is deficient in the lack of an effective method for creating a frozen tissue array for subsequent assaying. The present invention fulfills this longstanding need and desire in the art.

SUMMARY OF THE INVENTION

In one embodiment of the present invention, there is provided a method for creating a frozen tissue array, comprising the steps of selecting at least one frozen tissue core from a donor block; inserting each of the frozen cores into a compartment of a single recipient block, while the recipient block is held at a temperature below the freezing point of the tissue; adding an oil in a liquid form into the recipient block, where the oil has a freezing point lower than the freezing point of the tissue cores, where the oil is cooled to and is added at a temperature lower than the freezing point of said tissue but higher than the freezing point of said oil thereby keeping said tissue cores frozen; and cooling the recipient block containing the oil to a temperature of about equal to or below the freezing point of the oil, thereby freezing the oil, wherein the frozen oil locks the frozen cores in the recipient block to create the frozen tissue array without melting the frozen cores.

In another embodiment of the present invention there is provided a method for creating a frozen tissue array, comprising the steps of adding an oil in a liquid form into at least one compartment of a recipient block prior to inserting a frozen tissue core into the compartment; where the recipient block is held at a temperature below the freezing point of the frozen tissue core and the oil has a freezing point lower than the freezing point of the tissue core; where the oil is cooled to and is added at a temperature lower than the freezing point of the tissue core and less than or equal to the temperature of the recipient block but higher than the freezing point of the oil; selecting at least one frozen tissue core from a donor block, where the donor block is held at a temperature less than the freezing point of the tissue contained within the block and less than or equal to the temperature of the recipient block; inserting each of the frozen tissue cores into a compartment of a single recipient block containing the oil thereby keeping the tissue cores frozen; and cooling the recipient block containing the oil and the frozen tissue cores to a temperature of about equal to or below the freezing point of the oil, thereby freezing the oil, wherein the frozen oil locks the frozen cores in the recipient block to create the frozen tissue array without melting the frozen cores.

In yet another embodiment of the present invention, there is provided a method for preparing tissue for assays, comprising the steps of preparing a frozen tissue array by either of the methods disclosed supra; cutting sections from said array; and assaying said sections.

Other and further aspects, features, and advantages of the present invention will be apparent from the following description of the presently preferred embodiments of the invention given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

In one embodiment of the present invention, there is provided a method for creating a frozen tissue array, comprising the steps of selecting at least one frozen tissue core from a donor block; inserting each of the frozen cores into a compartment of a single recipient block, while the recipient block is held at a temperature below the freezing point of the tissue; adding an oil in a liquid form into the recipient block, where the oil has a freezing point lower than the freezing point of the tissue cores, where the oil is cooled to and added at a temperature lower than the freezing point of said tissue but higher than the freezing point of said oil thereby keeping said tissue cores frozen; and cooling the recipient block containing the oil to a temperature of about equal to or below the freezing point of the oil, thereby freezing the oil, wherein the frozen oil locks the frozen cores in the recipient block to create the frozen tissue array.

In another embodiment of the present invention there is provided a method for creating a frozen tissue array, comprising the steps of adding an oil in a liquid form into at least one compartment of a recipient block prior to inserting a frozen tissue core into the compartment; where the recipient block is held at a temperature below the freezing point of the frozen tissue core and the oil has a freezing point lower than the freezing point of the tissue core; where the oil is cooled to and added at a temperature lower than the freezing point of the tissue core and less than the temperature of the recipient block but higher than the freezing point of the oil; selecting at least one frozen tissue core from a donor block, where the donor block is held at a temperature less than the freezing point of the tissue contained within the block and less than the temperature of the recipient block; inserting each of the frozen tissue cores into a compartment of a single recipient block containing the oil thereby keeping the tissue cores frozen; and cooling the recipient block containing the oil and the frozen tissue cores to a temperature of about equal to or below the freezing point of the oil, thereby freezing the oil, wherein the frozen oil locks the frozen cores in the recipient block to create the frozen tissue array.

Representative diameters for the frozen tissue core samples to be assayed are about 1.0 mm to about 3.0 mm in diameter, preferably about 2.5 mm to about 3.0 mm in diameter. The oil may have a freezing point as low as about −10° C. In an aspect of both of the embodiments disclosed supra, the compartments in the recipient mold may be formed by filling a tissue mold with embedding medium; where, the embedding medium is capable of being frozen therein and forming a recipient tissue block; placing a cryoarray device into the tissue mold containing the embedding medium but prior to freezing the embedding medium, freezing the embedding medium in the tissue mold around the cryoarray pins; and lowering the ejector plate to separate the cryoarray device from the frozen embedding medium so that the cryoarray pins create compartments into the recipient block upon separation of the cryoarray device from the recipient block. A representative example of the embedding medium is O.C.T.™ compound. The embedding medium is frozen at temperature of about −20° C. to about −80° C.

The cryoarray device has a mold plate having an upper and a lower surface; mold alignment pins to direct placement of the cryoarray device into the tissue mold where the mold alignment pins are perpendicularly attached to the lower surface of the mold plate. An ejector plate in the device has an upper surface and a lower surface where the plate has holes between the upper surface and the lower surface; ejector pins with ejector thumb pads attached to an upper surface of the pins and connected to the mold plate and the ejector plate, is capable of lowering and of raising the ejector plate. Cryoarray pins, operably connected to the mold plate, are equal in number to the holes in the ejector plate and are aligned with the holes in the ejector plate in order to move through the holes.

In yet another embodiment of the present invention, there is provided a method for preparing tissue for assays, comprising the steps of preparing a frozen tissue array by either of the methods disclosed supra; cutting sections from said array; and assaying said sections. Examples of tissue assays that can be hybridization, immunohistochemistry, in situ polymerase chain reaction and fluorescence in situ hybridization.

Provided herein is a method for forming frozen tissue arrays for subsequent analysis. When comparing a frozen tissue array prepared in this manner to a paraffin-embedded array, even if the number of specimens that can be analyzed per array is lower than that with paraffin tissue arrays, the frozen tissue array system provides a significant advantage. Because a core diameter of 3 mm is used in the instant frozen arrays, it may not be necessary to array more than one or two biopsies per specimen, thus increasing the efficiency in comparison with paraffin tissue arrays. Additional advantages of the instant frozen tissue arrays include, after sectioning of the array, the use of multiple fixatives to optimize immunohistochemistry (IHC) or in-situ hybridization (ISH) for target probe or antibody assays and the use of the very same samples on which immunohistochemistry or in-situ hybridization is carried out to extract RNA to make cDNA for gene microchip analysis. Embodiments of the present invention are better illustrated with reference to the Figures, however, such reference is not meant to limit the present invention in any fashion.

In the method disclosed herein frozen tissue core samples are placed in a recipient block formed of an embedding material. The recipient block may be formed in a manner standard in the art. A plastic mold for frozen tissue is filled with a liquid embedding medium to the fill line indicated on the tissue mold. A representative example of a tissue mold is Cryomold having 37 cm×24 cm dimensions (Simport, Montreal, Canada) and of an embedding medium is optimal cutting temperature compound or O.C.T.™ compound (SAKURA FINETEK, Torrance, Calif.). O.C.T.™ compound has a freezing point of 0° C. The embedding material is frozen to form the basic block.

Figure 1:
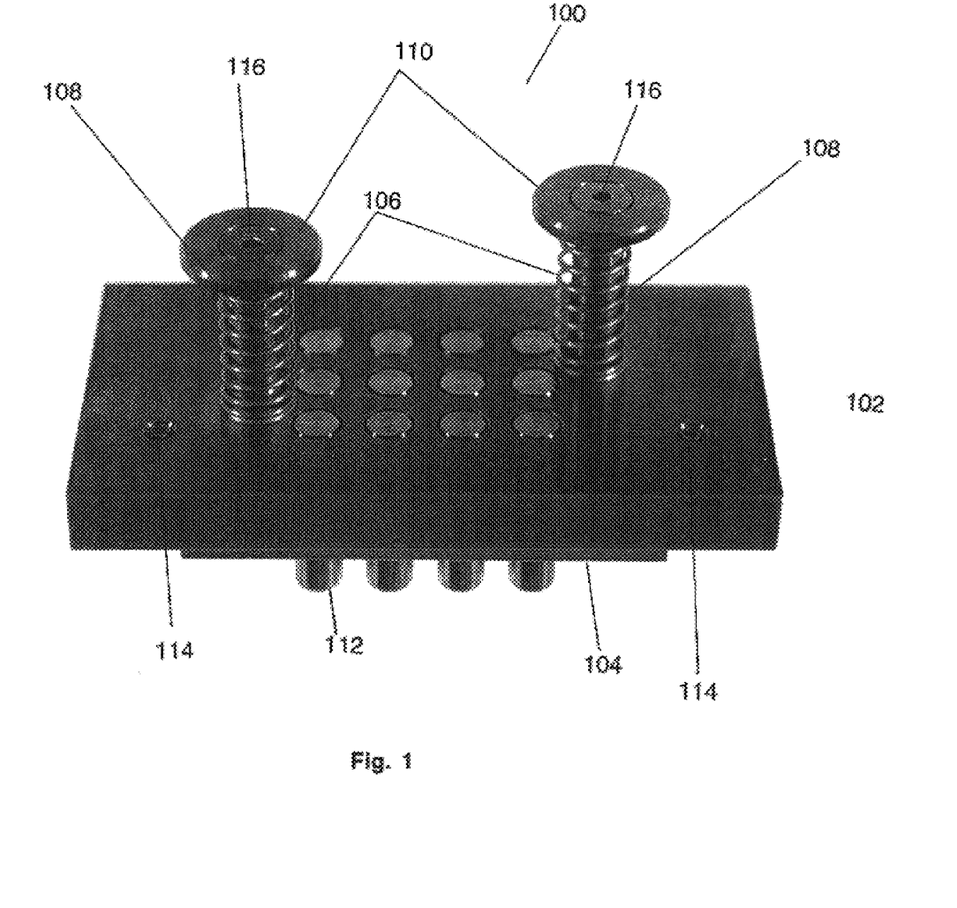
FIG. 1 shows an over view of the cryoarray apparatus 100, comprising a mold plate 102, an ejector plate 104, two ejector/guide springs 106, two ejector/guide pins 108, two ejector thumb pads 110, twelve cryoarray pins 112, two mold alignment pins 114, and two ejector screws 116.
Figure 2:
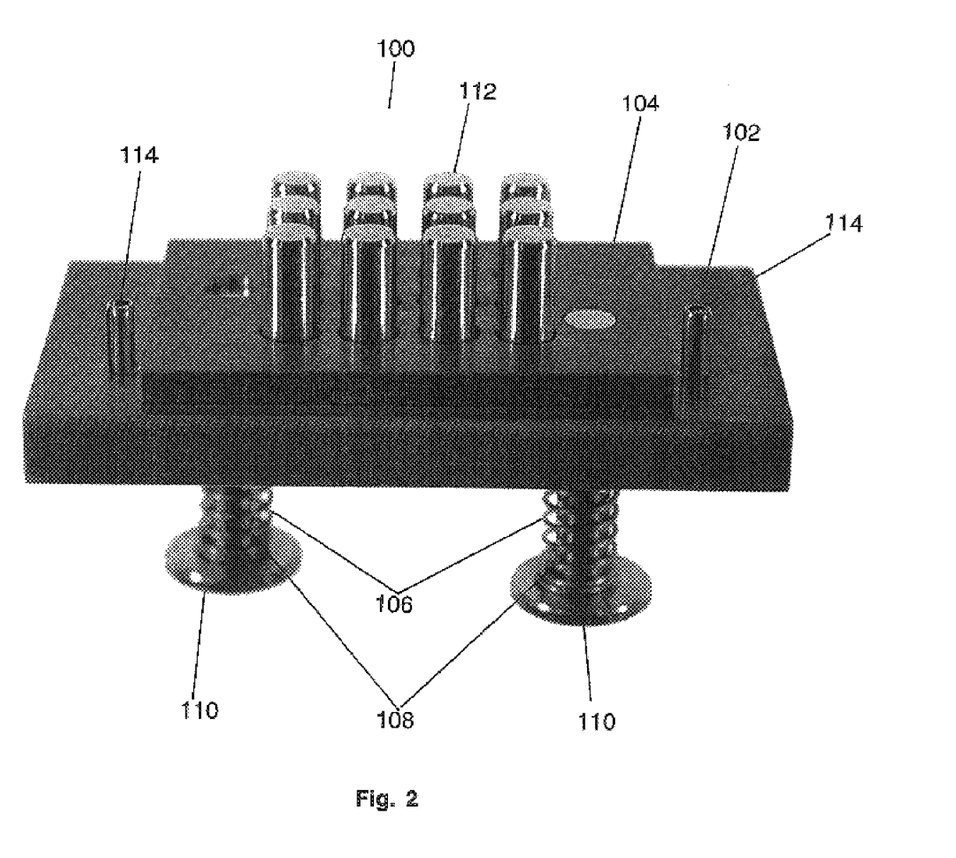
FIG. 2 shows another over view of the cryoarray apparatus 100 from a different angle, which is an upside-down position compared to the view in FIG. 1.
Figure 3:
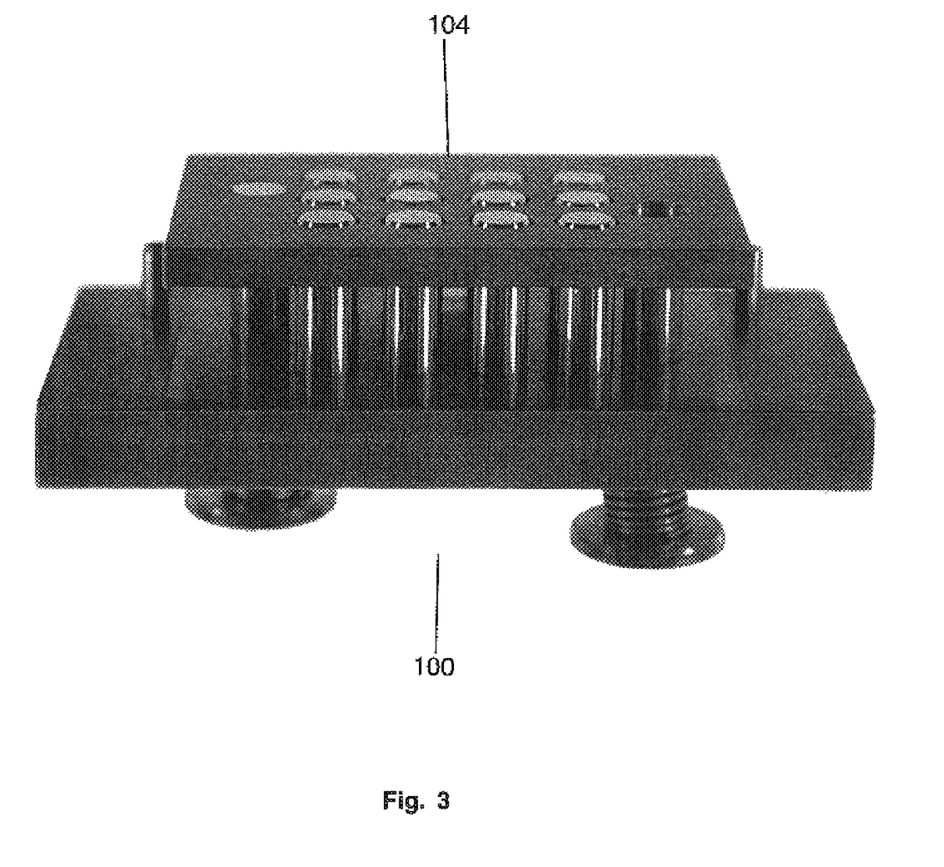
FIG. 3 shows the cryoarray apparatus 100 during the activation of the ejector plate 104.

The recipient block may be formed by use of a cryoarray device. A cryoarray device design is shown in FIGS. 1–3. The cryoarray apparatus 100 comprises a mold plate 102, an ejector plate 104, two ejector/guide springs 106, two ejector/guide pins 108, two ejector thumb pads 110, twelve cryoarray pins 112, two mold alignment pins 114, and two ejector screws 116. Furthermore, although the apparatus 100 depicted herein comprises twelve cryoarray pins 112, the number of pins in the cryoarray need not be limited to twelve, e.g., a forty-eight compartment cryoarray can increase the number of cores in a cryoarray, thereby increasing the size of the assay data set. The diameter of the cryoarray pins 112 is about 3 mm. Table 1 lists each component of the cryoarray as well as the material of which each component is made.

TABLE 1

Components of Cryoarray System 100

| Reference # | Title | Material | Quantity |
| --- | --- | --- | --- |
| 102 | Mold Plate | Brass | 1 |
| 104 | Ejector Plate | Brass | 1 |
| 106 | Ejector/Guide Spring | Stainless Steel | 2 |
| 108 | Ejector/Guide Pin | Stainless Steel | 2 |
| 112 | Cryoarray Pin (variable number) | Stainless Steel | 12 (as shown) |
| 114 | Mold Alignment Pin | Stainless Steel | 2 |
| 110 | Ejector Thumb Pad | Brass | 2 |
| 116 | Ejector Screw | Stainless Steel | 2 |

Figure 4:
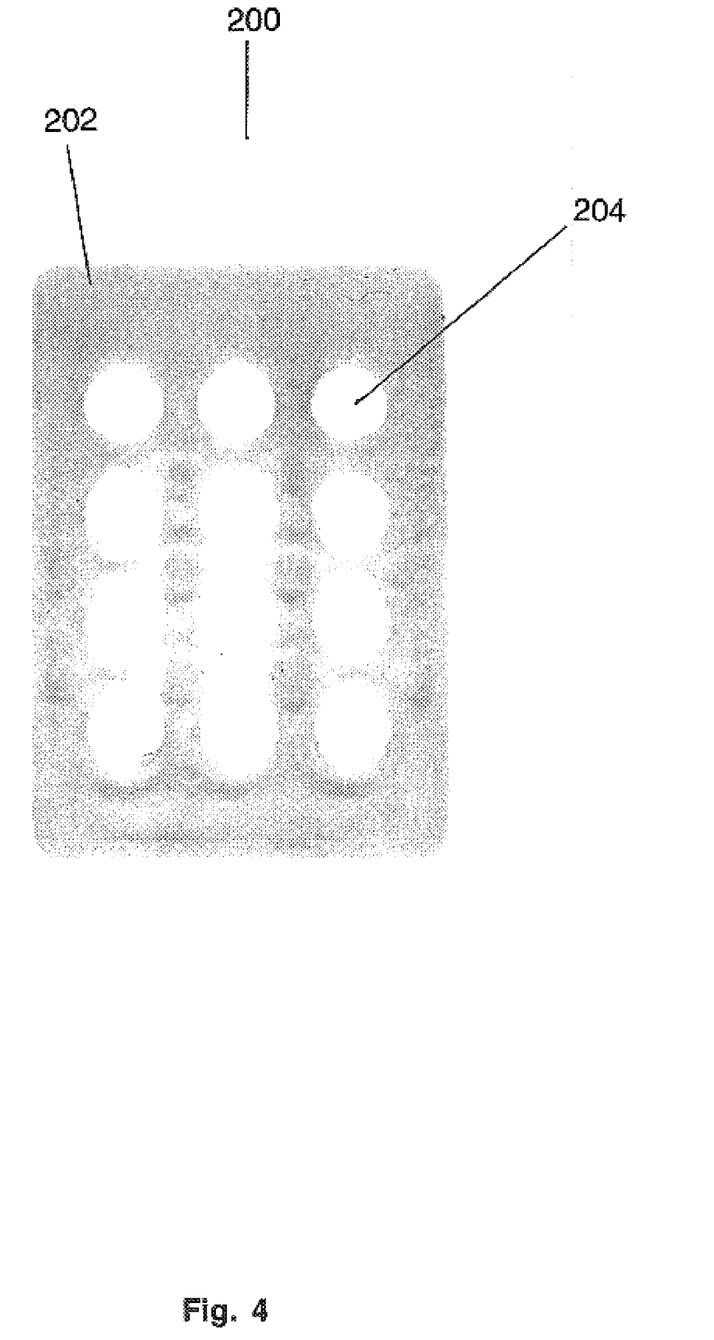
FIG. 4 shows the frame 202 with a twelve-hole grid 204 that forms the frozen tissue array 200.

With reference to FIG. 4 and continued reference to FIGS. 1–3 the cryoarray apparatus 100 is used with a tissue mold (not shown) to form a cryoarray or frozen tissue array system comprising a single recipient block 200 of arrayed multiple biopsies taken from embedded frozen tissues. The recipient block 200 is a frame of embedding compound 202 containing multiple preformed holes 204 having a diameter of about 3.0 mm.

The cryoarray apparatus 100 is placed into the Cryomold (not shown) as directed by the mold alignment pins 114. The cryoarray pins 112 displace the liquid embedding compound and create a grid of holes 204 framed by the embedding compound 202. The tissue mold containing the cryoarray 100 is then placed at about −20° C. to about −80° C. for about 15 minutes or until the liquid embedding compound is solidified and thus forms the recipient block in the cryoarray 200. Once the embedding compound is frozen, the ejector pins 108 on the cryoarray device 100 are depressed, activating the ejector plate 104 which lowers over the cryoarray pins 112. This releases the frozen recipient block in the cryoarray 200 which comprises the frozen embedding compound frame 202 having a grid of holes 204 equal to the number of cryoarray pins 112 that form the cryoarray or frozen tissue array 200.

Figure 5:
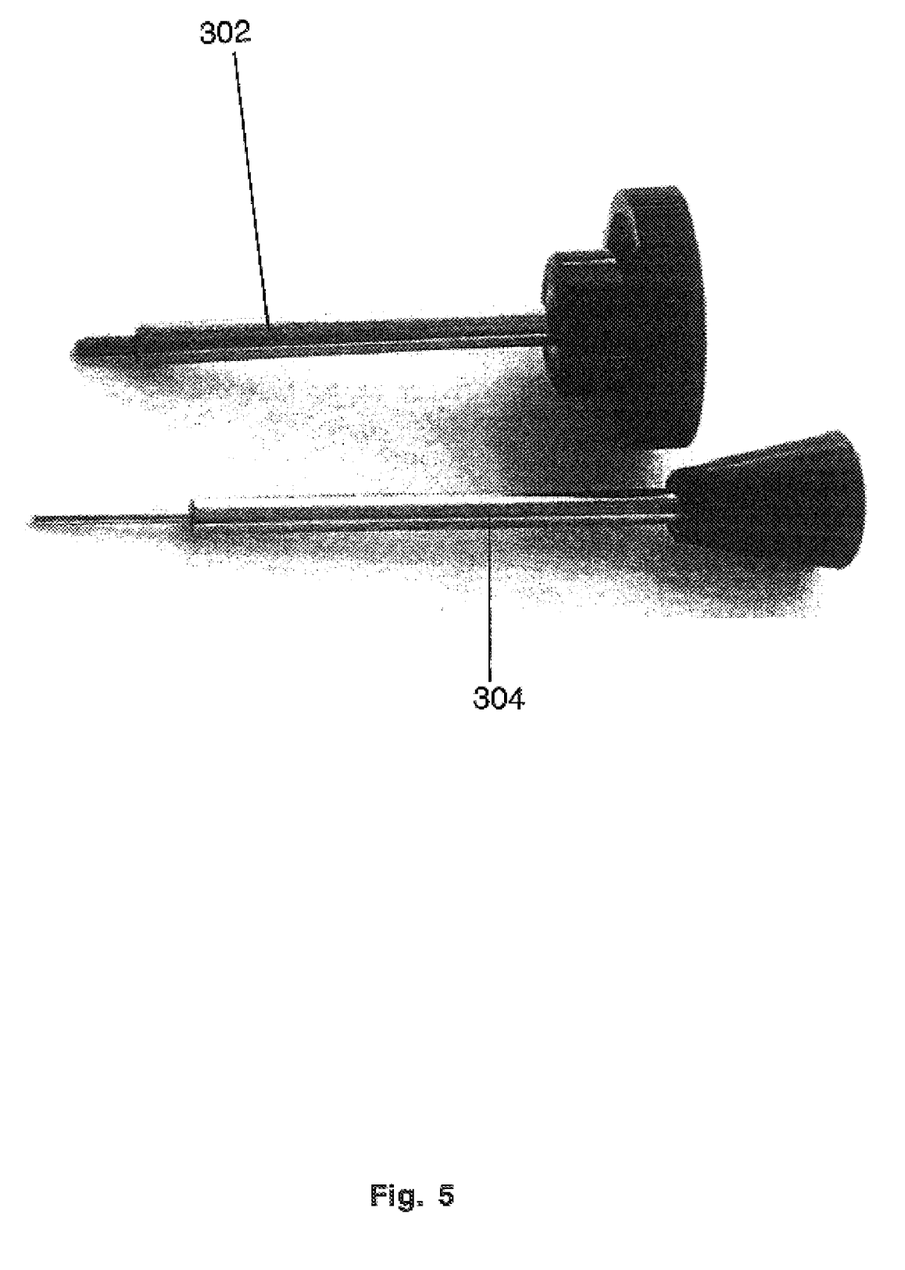
FIG. 5 shows a biopsy needle 302 of 3 mm diameter (top) and a piston 304 insertable into the core of the biopsy needle.
Figure 6:
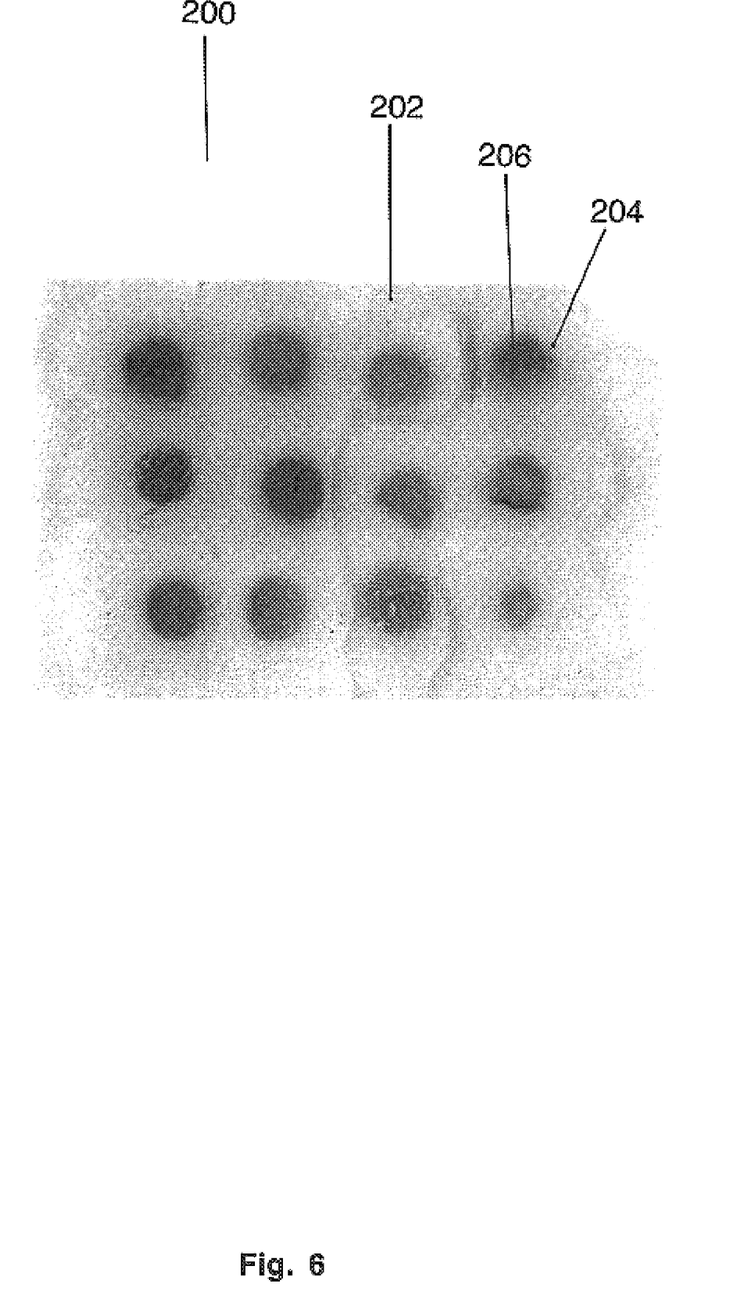
FIG. 6 shows the final form of the frozen tissue array 200 including frozen cores 206 taken from normal tissue donor blocks.

With reference to FIGS. 5 and 6 and continued reference to FIG. 4, a specifically designed core biopsy needle 302 of 3 mm diameter is used to punch core specimens 206 from identified areas of frozen donor tissue blocks (not shown). The strong core needle 302 punches a hole in the identified area of the donor block and the piston 304 is inserted into the core needle 302 in order to release the punched frozen specimen core 206 into one of the grid holes 204 of the recipient block 202 in the cryoarray 200 in a manner similar to and standard for paraffin-embedded tissues and known to one of ordinary skill in the art. The core samples 206 preferably have a diameter of about 2.5 mm to 3.0 mm. It is to be understood that when using the cryoarray 200, frozen cores of less than 1 mm in diameter usually become friable and can break apart. Thus, a particularly fine needle diameter may be optimal for removing a frozen core from donor blocks.

The frozen tissue core samples 206 are removed from a donor block (not shown) that is held at a temperature less than the frozen tissue and preferably equal or less than that of the recipient block. The core samples 206 are then locked in the recipient block 202 which is also held a temperature lower than the frozen tissue cores, e.g., between about −8° C. and −9° C., 206 thus insuring that the frozen tissue cores 206 remain frozen by adding an oil cooled to a temperature between about −8° C. and −9° C., which is also a temperature lower than the freezing point of the tissue but higher than the freezing point of the oil thereby keeping the tissue cores 206 frozen. The oil has a freezing point of as low as −10° C. and is used for locking the cores. An example of this oil is INSTRUMEDICS PROTECTIVE OIL® (Instrumedics, Hackensack, N.J.) and it is used for coating frozen blocks to prevent dehydration during long-term storage. The oil has a freezing point which is lower than the embedding compound used to make the recipient frame 202, e.g. INSTRUMEDICS PROTECTIVE OIL® is 10° C. lower than the surrounding O.C.T.™ compound. This property of the oil allows the frozen tissue cores 206 to be easily inserted into the compartments or grid holes 204 in the recipient block 202. After addition of the oil, the temperature of the entire frozen tissue array 200 is lowered to about −10° C. Alternatively, the oil is added to the compartments 204 of the recipient block 202 prior to inserting the frozen tissue cores into these compartments or grid holes 204 under the conditions described.

Figure 7:
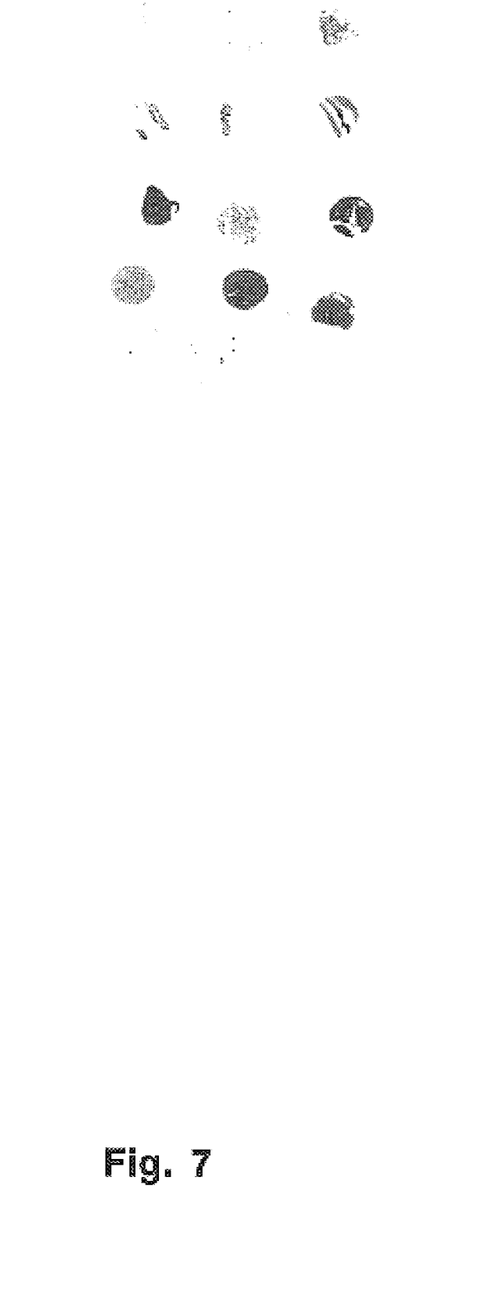
FIG. 7 shows a hematoxylin and eosin stained section used for morphological evaluation of the above normal tissue array.

The further processing of the cryoarray 200 follows the general guidelines for embedded frozen tissue samples, particularly for samples embedded in O.C.T.™. Frozen sections are generated using a tape-based sectioning system (Instrumedics, Hackensack, N.J.). Sections cut from the frozen tissue or cryoarray 200 allow parallel detection of DNA (e.g. by fluorescence in-situ hybridization), RNA (e.g. by mRNA ISH) or protein (e.g. by immunohistochemical analysis) targets in each of the specimens 206 in the frozen tissue array or cryoarray 200. FIG. 7 depicts a hematoxylin and eosin stained section of the frozen tissue specimen 206.

Cell proliferation, differentiation, death and genomic integrity is controlled by a multitude of genes and signaling pathways in cancer development. Through new techniques, such as cDNA microarrays, the expression of thousands of genes can be measured in a single experiment. As such, analysis of thousands of specimens from patients at different stages of disease can be comprehensively surveyed. The potential uses of the cryoarray disclosed herein include analyzing molecular basis of tumor progression; obtaining molecular profiling of thousands of tumors with hundreds of biomarkers; validation of cDNA microarray screening data; rapid translation of results from cell line and animal models to human cancer; evaluation of the diagnostic, prognostic and therapeutic potential of newly discovered genes and molecules; testing and optimization of probes and antibodies; improved utilization of pathology archives and tissue banks; and international, large scale collaborations for multi-center molecular profiling of tumors.

The following references were cited herein.

1. Kononen et al. Nature Medicine 4: 844–847 (1998).
2. Bubendorf et al. Cancer Research 59: 803–806 (1999).
3. Ornstein, L. and Schiller, B. J. Cell Biol. 515a, (1986)

Any patents or publications mentioned in this specification are indicative of the levels of those skilled in the art to which the invention pertains. These patents and publications are herein incorporated by reference to the same extent as if each individual publication was indicated specifically and individually to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for creating a frozen tissue array, comprising the steps of:
    selecting at least one frozen tissue core from a frozen tissue embedded within a donor block, said donor block held at a temperature less than the freezing point of said tissue embedded within said block;
    inserting each of said at least one frozen core into a compartment of a single recipient block, wherein said recipient block is held at a temperature below the freezing point of said tissue;
    adding an oil in a liquid form into said recipient block, wherein said oil has a freezing point lower than the freezing point of said tissue cores, said oil cooled to and added at a temperature lower than the freezing point of said tissue but higher than the freezing point of said oil thereby keeping said tissue cores frozen; and
    cooling said recipient block containing said oil to a temperature of about equal to or below the freezing point of said oil, thereby freezing said oil, wherein the frozen oil locks said frozen cores in said recipient block to create said frozen tissue array.

2. The method of claim 1, wherein said tissue core has a diameter or about 1.0 mm to about 3.0 mm.

3. The method of claim 2, wherein said tissue core has a diameter of about 2.5 mm to about 3.0 mm.

4. The method of claim 1, wherein said oil has a freezing point as low as about −10° C.

5. The method of claim 1, wherein the formation of compartments in said recipient block comprises the steps of:
    filling a tissue mold with embedding medium; said embedding medium capable of being frozen therein, said frozen embedding medium forming a recipient tissue block;
    placing a cryoarray device into said tissue mold containing said embedding medium but prior to freezing said embedding medium, said cryoarray device comprising:
        a mold plate having an upper and a lower surface;
        mold alignment pins to direct placement of the cryoarray device into said tissue mold, said mold alignment pins perpendicularly attached to the lower surface of said mold plate,
        an ejector plate having an upper surface and a lower surface, said plate comprising holes between said upper surface and said lower surface;
        ejector pins, said ejector pins comprising ejector thumb pads attached to an upper surface of said pins, said ejector pins connecting said mold plate and said ejector plate, wherein said ejector pins are capable of lowering and of raising said ejector plate; and
        cryoarray pins, said cryoarray pins connected operably to said mold plate and equal in number to said holes in said ejector plate and aligned with said holes in said ejector plate wherein said cryoarray pins move through said holes;
    freezing said embedding medium in said tissue mold around said cryoarray pins; and
    lowering said ejector plate to separate said cryoarray device from said frozen embedding medium; said cryoarray pins creating compartments into said recipient block upon separation of said cryoarray device from said recipient block.

6. The method of claim 5, wherein said embedding material is frozen at a temperature of about −20° C. to about −80° C.

7. The method of claim 5, wherein said embedding medium is O.C.T.™ compound.

8. A method for preparing tissue for assays, comprising the steps of:
    preparing a frozen tissue array as in claim 1;
    cutting sections from said array; and
    assaying said sections.

9. The method of claim 8, wherein said tissue assay is selected from the group consisting of morphologic evaluation, in situ hybridization, immunohistochemistry, in situ polymerase chain reaction and fluorescence in situ hybridization.

10. A method for creating a frozen tissue array, comprising the steps of:
    adding an oil in a liquid form into at least one compartment of a recipient block prior to inserting a frozen tissue core into said compartment; wherein said recipient block is held at a temperature below the freezing point of said frozen tissue core; said oil having a freezing point lower than the freezing point of said tissue core; wherein said oil is cooled to and added at a temperature lower than the freezing point of said tissue care and less than or equal to the temperature of said recipient block but higher than the freezing paint of said oil;
    selecting at least one frozen tissue core from a frozen tissue embedded within a donor block, said donor block held at a temperature less than the freezing point of said tissue contained within said block and less than or equal to the temperature of said recipient block;
    inserting each of said at least one frozen tissue core into said compartment of a single recipient block containing said oil thereby keeping said tissue cores frozen; and cooling said recipient block containing said oil and said frozen tissue cores to a temperature of about equal to or below the freezing point of said oil, thereby freezing said oil, wherein the frozen oil locks said frozen cores in said recipient block to create said frozen tissue array.

11. The method of claim 10, wherein said tissue core has a diameter of about 1.0 mm to about 3.0 mm.

12. The method of claim 11, wherein said tissue core has a diameter of about 2.5 mm to about 3.0 mm.

13. The method of claim 10, wherein said oil has a freezing point as low as about −10° C.

14. The method of claim 10, wherein the formation of compartments in said recipient block comprises the steps of:
  filling a tissue mold with embedding medium; said embedding medium capable of being frozen therein, said frozen embedding medium forming a recipient tissue block;
  placing a cryoarray device into said tissue mold containing said embedding medium but prior to freezing said embedding medium, said cryoarray device comprising:
    a mold plate having an upper and a lower surface;
    mold alignment pins to direct placement of the cryoarray device into said tissue mold, said mold alignment pins perpendicularly attached to the lower surface of said mold plate,
    an ejector plate having an upper surface and a lower surface, said plate comprising holes between said upper surface and said lower surface;
    ejector pins, said ejector pins comprising ejector thumb pads attached to an upper surface of said pins, said ejector pins connecting said mold plate and said ejector plate, wherein said ejector pins are capable of lowering and of raising said ejector plate; and
    cryoarray pins, said cryoarray pins connected operably to said mold plate and equal in number to said holes in said ejector plate and aligned with said holes in said ejector plate wherein said cryoarray pins move through said holes;
  freezing said embedding medium in said tissue mold around said cryoarray pins; and
  lowering said ejector plate to separate said cryoarray device from said frozen embedding medium; said cryoarray pins creating compartments into said recipient block upon separation of said cryoarray device from said recipient block.

15. The method of claim 14, wherein said embedding material is frozen at a temperature of about −20° C. to about −80° C.

16. The method of claim 14, wherein said embedding medium is O.C.T.™ compound.

17. A method for preparing tissue for assays, comprising the steps of:
  preparing a frozen tissue array as in claim 10;
  cutting sections from said array; and
  assaying said sections.

18. The method of claim 8, wherein said tissue assay is selected From the group consisting of morphologic evaluation, in Situ hybridization, immunohistochemistry, in situ polymerase chain reaction and fluorescence in situ hybridization.

* * * * *